US00PP10620P

United States Patent [19]

Delbard

[11] Patent Number: Plant 10,620

[45] Date of Patent: Sep. 29, 1998

[54] HYBRID TEA ROSE PLANT NAMED 'DELBLACREM'

[75] Inventor: Guy Delbard, Hyeres, France

[73] Assignee: Societe Anonyme Des Pepinieres et Roseraies Georges Delbard, Commentry, France

[21] Appl. No.: 800,059

[22] Filed: Feb. 14, 1997

[30] Foreign Application Priority Data

Dec. 19, 1996 [FR] France ..... 15220

[51] Int. Cl.[6] ..... A01H 5/00

[52] U.S. Cl. ..... Plt./11

[58] Field of Search ..... Plt./14, 15, 11

[56] References Cited

PUBLICATIONS

UPOV–ROM, 1997 Apr., Plant Variety Database, GTIJouve Retrieval Software, citation for 'Delblacrem'.

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided that abundantly forms attractive double flowers that are ivory in coloration. The buds are very long in configuration and tend to open slowly. The blossoms exhibit a long vase life. The plant exhibits an upright growth habit, forms vigorous vegetation, and is particularly well suited for greenhouse forcing for cut flower production. Additionally, the plant is resistant to diseases when grown under greenhouse conditions.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) was the 'Krilamy' variety (non-patented) in the United States). The male parent (i.e., the pollen parent) was the 'Pekougel' variety. The parentage of the new variety can be summarized as follows:

'Krilamy'×'Pekougel'.

The seeds resulting from the above pollination were sown and 382 small plantlets were obtained which were physically and biologically different from each other. Selective study resulted in the identification of a single plant of the new variety.

It was found through careful study that the new variety of the present invention exhibits the following combination of characteristics:

(a) from a physical point of view forms green mature wood, assumes an upright growth habit, and forms attractive long-lasting ivory double flowers having consistent petals, and (b) from the biological point of view forms vigorous vegetation, produces flowers in abundance, exhibits the ability readily to be forced, and is resistant to diseases when grown under greenhouse conditions.

The new variety well meets the needs of the horticultural industry and is particularly well suited for growing in the greenhouse for the production of attractive long-lasting cut flowers that are ivory with pale amber coloration at the center and sometimes with a fine pink line on the margins depending upon the environmental conditions that are encountered.

The new variety can be readily distinguished from other varieties in view of the combination of characteristics described herein. It exhibits long and straight stems, rigid and straight peduncles, a good ability to be forced under greenhouse conditions, and a long vase life for its distinctive ivory blossoms.

For instance, the new variety of the present invention can be distinguished from the 'Krilamy' parent, with the new variety exhibiting ivory blossoms which convey a pale amber impression and the 'Krilamy' variety exhibiting blossoms that are more white. Also, the 'Pekougel' parent exhibits pink bicolored blossoms which are totally different in coloration than those of the new variety, as well as a different bud configuration.

The new variety has been found to undergo asexual propagation and can be readily reproduced by conventional routes, such as budding (i.e., eye grafting) and tissue culture. This asexual reproduction by budding and tissue culture as performed at Hyéres, France, has demonstrated that the characteristics of the new variety are strictly transmissible from one generation to another and are firmly fixed.

The new variety has been named the 'Delblacrem' variety.

BRIEF DESCRIPTION OF THE PHOTOGRAPH

The accompanying photograph shows as nearly true as it is reasonably possible to make the same in a color illustration of this character typical specimens of the plant parts of the new variety. The rose plants of the new variety were grown under glass in the South of France.

FIG. 1—illustrates a specimen of a leaf with five leaflets—plan view—upper surface;

FIG. 2—illustrates a specimen of a leaf with five leaflets—plan view—under surface;

FIG. 3—illustrates a specimen of a leaf with seven leaflets—plan view—upper surface;

FIG. 4—illustrates a specimen of a leaf with seven leaflets—plan view—under surface;

FIG. 5—illustrates a specimen of a young shoot;

FIG. 6—illustrates a specimen of a flowering stem;

FIG. 7—illustrates a specimen of a floral bud as the opening of the sepals begins;

FIG. 8—illustrates a specimen of a floral bud as the opening of the sepals progresses;

FIG. 9—illustrates a further specimen of a floral bud as the opening of the sepals progresses;

FIG. 10—illustrates a specimen of a floral bud at the opening of the petals;

FIG. 11—illustrates a specimen of a flower at an early stage in the course of opening;

FIG. 12—illustrates a further specimen of a flower in the course of opening;

FIG. 13—illustrates a specimen of a flower in a further stage of opening;

FIG. 14—illustrates a specimen of an open flower plan view—obverse;

FIG. 15—illustrates a specimen of an open flower plan view—reverse;

FIG. 16—illustrates a specimen of a fully open flower—plan view—reverse;

FIG. 17—illustrates a specimen of a fully open flower—plan view—obverse;

FIG. 18—illustrates a specimen of a floral receptacle showing the arrangement of the pistils (stamens removed); and FIG. 19—illustrates a specimen of a floral receptacle showing the arrangement of the stamens and pistils.

DETAILED DESCRIPTION

The chart used in the identification of the colors is that of The Royal Horticultural Society (R.H.S. Colour Chart). The description is based on the observation of plants grown under glass in the South of France. The coloration in common terms sometimes also is provided.

Class: Hybrid Tea.

Plant:

*Height.*—Plants which were pruned to a height of 1 m. produce floral stems having a length of approximately 60 to 120 cm., and an average length of approximately 90 cm.

*Habit.*—Upright.

Branches:

*Color.*—Young shoots: when approximately 20 cm. long, exhibit a green coloration, Yellow-Green Group 146C with sometimes reddish coloration on one side depending upon the environment. Floral stems: Yellow-Green Group 146C. Mature wood: Yellow-Green Group 146B.

*Thorns.*—Configuration: concave and nearly straight on the upper edge and concave on the under edge. Quantity, length and frequency: on a typical stem having a length of 10 cm., there commonly are a few short prickles of less than 5 mm., and approximately 6 to 10 longer prickles of more than 5 mm. The prickles commonly are approximately 2 to 13 mm. in length and average approximately 10 mm. in length on floral stems and approximately 9 mm. in length on mature wood. The stems commonly are smooth. Color: on young shoots of approximately 30 cm. in length, the thorns are Yellow-Green Group 152D but more pale with some reddish coloration when cool, and on floral stems the coloration of the thorns is Yellow-Green Group 152D but more pale with reddish coloration when cool, and on mature wood the coloration of the thorns is Greyed-Orange Group 165A (havana brown).

*Leaves.*—Number: typical for the class. Size: medium to large. Stipules: adnate, small to medium, and normal for the class.

*Leaflets.*—Number: sometimes 3, and commonly 5 or 7. Size: large to very large. Shape: obtuse to rounded at the base of the terminal leaflet and slightly cordate at the intersection with the peduncle; slightly concave in the cross-section; and very weak in margin undulation. Serration: present, single, irregular, and not strongly marked. General appearance: thin, weak, with a medium glossiness on the upper surface of the leaflets. Petiole: the inner surface is grooved with non-glandular edges. Petiole color on young shoot: purple with green coloration on the inner surface and Yellow-Green Group 146D on the outer surface. Petiole color on floral stem: bronze green coloration on the inner surface and Yellow-Green Group 146D on the outer surface. Petiole color on mature wood: Yellow-Green Group 146D on inner surface, and Yellow-Green Group 146D on outer surface. Petiole length of terminal leaflet: for a leaf having five leaflets approximately 12 to 19 mm., approximately 16 mm. on average, with a standard deviation of 2 mm. Terminal leaflet length: approximately 53 to 120 mm., approximately 70 mm. on average, with a standard deviation of 15 mm. Terminal leaflet width: approximately 38 to 70 mm., approximately 48 mm. on average, with a standard deviation of 10 mm. Terminal leaflet shape at base: obtuse to rounded and slightly cordate at the intersection with the petiole. Leaflet color of young shoot: on the upper surface Green Group 137A in the center with bronze coloration on the sides and red serration on the tip, and on the under surface Yellow-Green Group 147B and green with reddish coloration on the tip. Leaflet color on floral stem: Yellow-Green Group 147A on the upper surface and Yellow-Green Group 148B to 148C on the under surface. Leaflet color of mature wood: Yellow-Green Group 147A to 147B on the upper surface, and Yellow-Green Group 147C on the under surface.

Inflorescence:

*Number of Flowers.*—Generally one per stem when grown under forced greenhouse conditions.

*Peduncle.*—Erect, stiff, Yellow-Green Group 146B in coloration with some hairs and smooth pink prickles of approximately 2 to 6 mm. in length, and commonly approximately 14 to 17 cm. in length (approximately 15 cm. in length on average).

*Sepals.*—configuration: there are 5 sepals. Commonly 2 sepals possess no extensions, commonly 2 sepals possess medium-to-long extensions, and commonly one sepal possesses a very long extension and sometimes even resembles a leaflet (See, for instance, FIG. 16). The sepal length commonly is 65 mm. on average. Color: Yellow-Green Group 147A on the upper surface and Yellow-Green Group 147B on the under surface.

*Buds.*—Shape: ovate. Size before calyx breaks: the bud lengths commonly are approximately 28 to 30 mm., with an average length of approximately 28 mm. Color as calyx breaks: commonly 2 petals from the second row are ivory with a green coloration and a small pink edge on the margin, and commonly two other petals from that row are ivory, Yellow Group 11D with some pinkish coloration. Size after calyx breaks: the bud lengths are approximately 52 to 70 mm., with an average length of approximately 60 mm. Color after calyx breaks: inside: ivory sometimes with pinkish coloration depending on the light and temperature. outside: ivory, Yellow Group 11D with some pale amber coloration.

*Flower.*—Time: medium flowering. Shape: double. Form: round to irregularly rounded when viewed from above, convex at the upper part when viewed from the side, and convex at the lower part when viewed from the side. Diameter: medium to large, approximately 9.5 to 11.5 cm., and approximately 10 cm. on average, with a standard deviation of 0.5 cm. Petal number: commonly approximately 28 to 40, and an average of approximately 35. Petal size (second row from outside): the length is approximately 52 to 70 mm. with a mean of approximately 56 mm., and a standard deviation of 0.4 mm.; and the width is approximately 56 to 70 mm. with a mean of approximately 60 mm., and a standard deviation of 0.4 mm. Petal shape: nearly rounded with medium reflexing and medium undulation of the margin. Petal color: The following description of a nearly fully open flower was made while observing a rose grown in the greenhouse during November which had been undergoing opening for 3 days. Petal color (middle zone): on the inner surface ivory, Yellow Group 11D to 11C towards the point of attachment, and on the outer surface ivory, Yellow Group 11D. petal color (marginal zone): on the inner surface white sometimes with pinkish coloration, Red Group 49C to 49D depending upon the temperature and the amount of light, and on the outer surface white sometimes with pinkish coloration Red Group 49C to 49D depending upon the temperature and the amount of light. Petal spot at base: very small. color of spot inner side: Yellow Group 4B. color of spot outer side: extremely small and Yellow Group 4C. Stamens: approximately 45 in number and are somewhat regularly arranged around the pistils. Filaments: long and Green-Yellow Group 1D in coloration. Anthers: medium in size, each opens at approximately the same time, and the immature coloration is yellow, Yellow-Orange Group 15C. Pollen: sparse in quantity and Yellow Group 4D in coloration. Pistils: approximately 40 in number. Styles: medium in length and Yellow Group 4D in coloration. Stigmas: Yellow Group 8C, and generally extend to slightly below the height of the anthers. Hips: in longitudinal section in the shape of a pitcher, and approximately 25 mm. in diameter. Seeds: small to medium in size, commonly approximately 10 to 22 in. in number with the average number being approximately 15. Petal drop: petals detach cleanly. Fragrance: light. Lasting quality: long. When cut and placed in a vase, the flowers commonly last approximately 10 to 15 days.

Development:

*Vegetation.*—Vigorous.

*Blooming.*—Abundant and almost continuous. Under greenhouse growing conditions at Hyéres, France, approximately 120 blooms commonly are produced per square meter per year.

*Aptitude to forcing.*—Good.

*Resistance to diseases.*—Good under greenhouse conditions, and sensitive to powdery mildew when grown outdoors.

I claim:

1. A new and distinct variety of Hybrid Tea rose plant characterized by the following combination of characteristics:

(a) from a physical point of view forms green mature wood, assumes an upright growth habit, and forms attractive long-lasting ivory double flowers having consistent petals, and (b) from the biological point of view forms vigorous vegetation, produces flowers in abundance, exhibits the ability readily to be forced, and is very resistant to diseases when grown under greenhouse conditions;

substantially as herein shown and described.

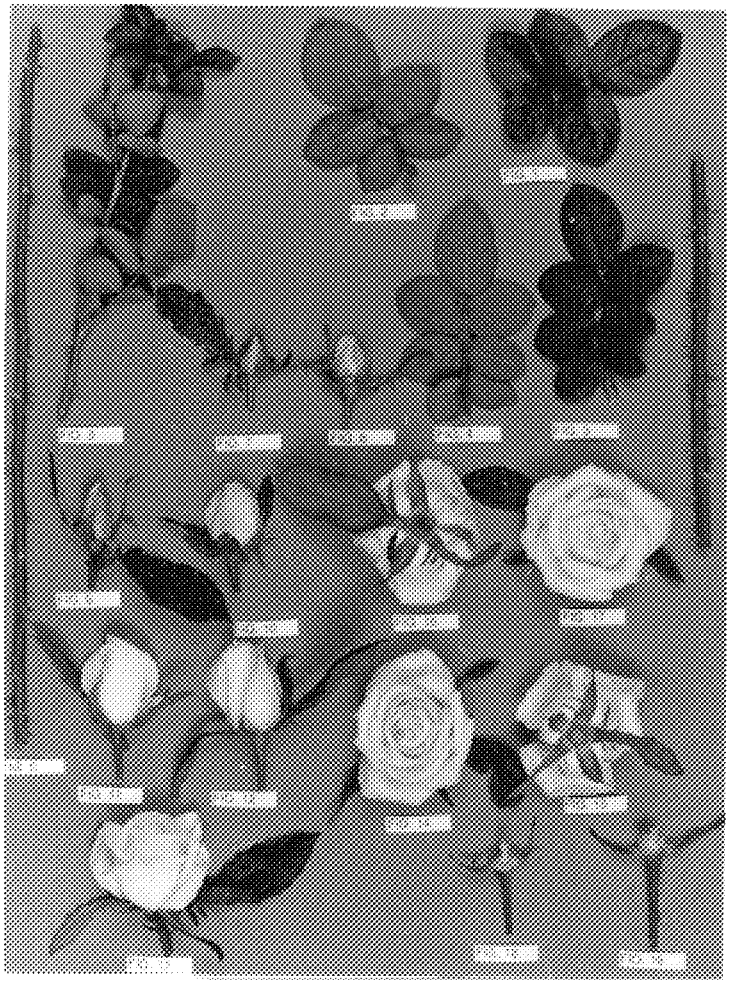

* * * * *